United States Patent
Brubaker et al.

(10) Patent No.: US 10,358,268 B2
(45) Date of Patent: Jul. 23, 2019

(54) OPENING COVER

(71) Applicant: Stryker Corporation, Kalamazoo, MI (US)

(72) Inventors: Michael T. Brubaker, Vicksburg, MI (US); Nathan Wray Matheny, Portage, MI (US); Kurosh Nahavandi, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/477,539

(22) Filed: Apr. 3, 2017

(65) Prior Publication Data

US 2017/0291742 A1 Oct. 12, 2017

Related U.S. Application Data

(60) Provisional application No. 62/320,100, filed on Apr. 8, 2016.

(51) Int. Cl.
*B65D 43/18* (2006.01)
*B65D 43/00* (2006.01)
*B65D 51/04* (2006.01)

(52) U.S. Cl.
CPC .................. *B65D 43/00* (2013.01)

(58) Field of Classification Search
CPC ......... B65D 43/18; B65D 43/26; B65D 43/00
USPC ...................... 220/816, 254.4, 813
See application file for complete search history.

(56) References Cited

U.S. PATENT DOCUMENTS

| | | | | |
|---|---|---|---|---|
| 365,232 A * | 6/1887 | Bingham | ................. | F16J 13/02 |
| | | | | 220/327 |
| 544,409 A * | 8/1895 | Jauch | ................... | B65F 1/1623 |
| | | | | 220/816 |
| 905,362 A * | 12/1908 | Pratt | ..................... | B65D 35/42 |
| | | | | 220/291 |
| 2,439,978 A * | 4/1948 | Konchan | .............. | E05B 17/185 |
| | | | | 220/253 |
| 2,547,353 A * | 4/1951 | Wiinikka | .............. | B65D 43/14 |
| | | | | 220/375 |
| 2,846,112 A * | 8/1958 | Eisenman | ................ | B65F 1/16 |
| | | | | 220/813 |
| 2,886,393 A * | 5/1959 | Tonning | ................. | A47G 33/00 |
| | | | | 206/19 |
| 2,923,430 A * | 2/1960 | Stengele | ............ | A47J 27/0817 |
| | | | | 220/264 |
| 2,965,260 A * | 12/1960 | Padykula | .............. | B65D 55/16 |
| | | | | 220/291 |
| 3,262,227 A * | 7/1966 | Pentecost | .............. | A62B 13/00 |
| | | | | 16/231 |

(Continued)

FOREIGN PATENT DOCUMENTS

JP  2003153748 A  5/2003

*Primary Examiner* — J. Gregory Pickett
*Assistant Examiner* — Niki M Eloshway
(74) *Attorney, Agent, or Firm* — Warner Norcross + Judd LLP

(57) ABSTRACT

A medical apparatus that includes an apparatus body that has a surface with an opening and a cover coupled to the apparatus body about an axis of rotation angled to the surface. The cover is operable to rotate about the axis of rotation to move between a first position wherein the cover closes the opening and a second position wherein the cover is moved to allow access to the opening.

23 Claims, 3 Drawing Sheets

(56) References Cited

U.S. PATENT DOCUMENTS

| | | | | |
|---|---|---|---|---|
| 4,106,664 A | * | 8/1978 | Renk | B65D 39/00 |
| | | | | 220/315 |
| 5,175,918 A | * | 1/1993 | Christopher | B65D 43/18 |
| | | | | 220/823 |
| 5,244,326 A | * | 9/1993 | Henriksen | F16B 37/145 |
| | | | | 411/180 |
| 5,350,264 A | * | 9/1994 | Stencel | F16B 19/1063 |
| | | | | 411/38 |
| 5,531,541 A | * | 7/1996 | Clover | E02D 29/1418 |
| | | | | 220/816 |
| 5,752,795 A | | 5/1998 | D'Adamo | |
| 5,921,425 A | * | 7/1999 | Markey | B65D 47/265 |
| | | | | 215/236 |
| 5,997,229 A | | 12/1999 | Akers | |
| 6,012,889 A | | 1/2000 | Robbins et al. | |
| 6,024,217 A | * | 2/2000 | Ponsi | A61B 50/36 |
| | | | | 206/370 |
| 6,401,958 B1 | * | 6/2002 | Foss | F16J 13/06 |
| | | | | 220/320 |
| 7,258,245 B2 | * | 8/2007 | Bauer | B60K 15/0406 |
| | | | | 220/211 |
| 7,341,398 B2 | * | 3/2008 | Johnson | E02D 29/1418 |
| | | | | 137/371 |
| D609,082 S | | 2/2010 | Camisasca et al. | |
| 7,938,282 B1 | * | 5/2011 | Hawry | B65D 41/0485 |
| | | | | 215/305 |
| 2008/0169299 A1 | * | 7/2008 | Simmons | B65D 17/16 |
| | | | | 220/816 |
| 2009/0145904 A1 | * | 6/2009 | Guidry, Jr. | B01J 3/03 |
| | | | | 220/323 |
| 2016/0016163 A1 | * | 1/2016 | Warden | B01L 3/527 |
| | | | | 422/547 |

\* cited by examiner

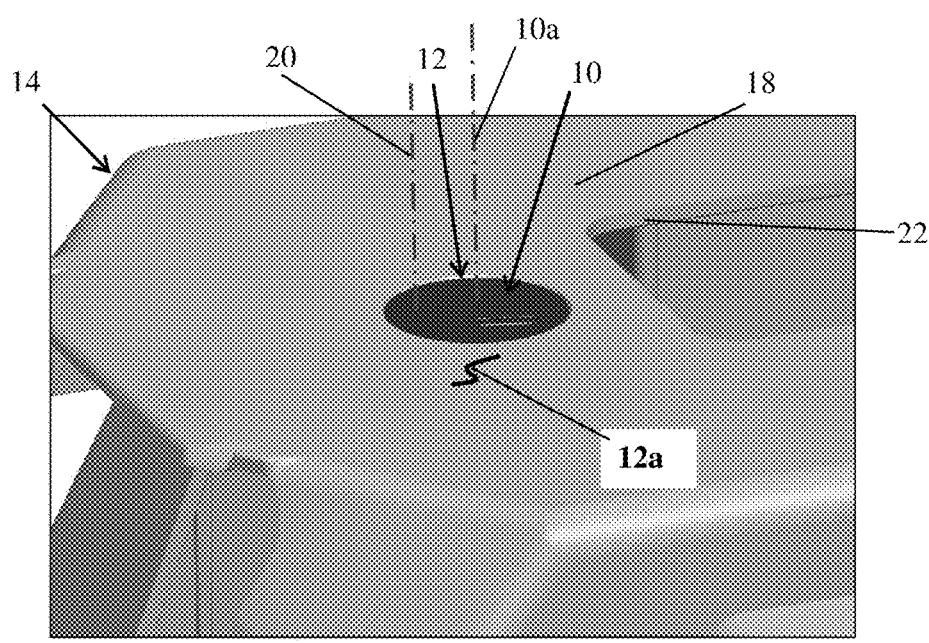
FIG. 1
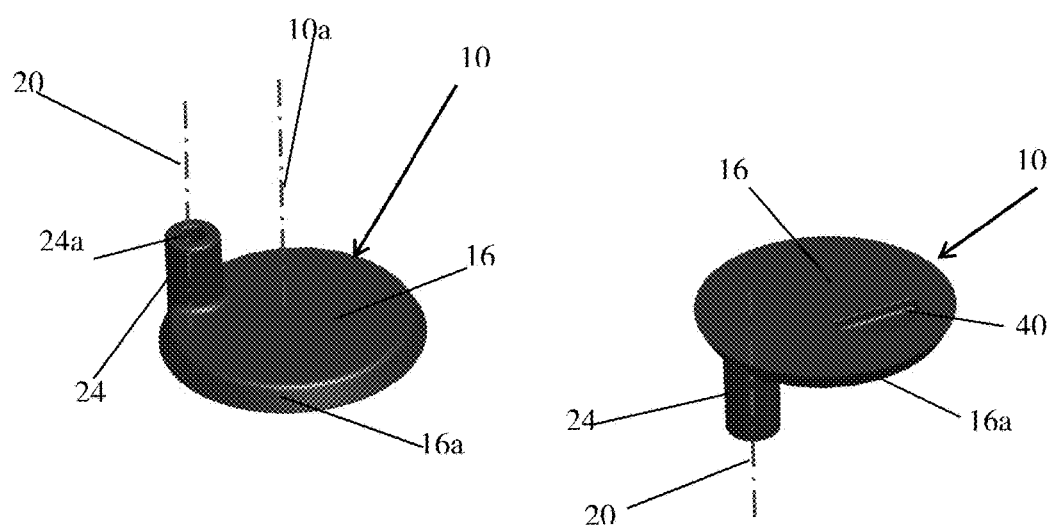
FIG. 3
FIG. 2

OPENING COVER

CROSS-REFERENCE TO RELATED APPLICATIONS

This application claims the benefit of U.S. provisional patent application Ser. No. 62/320,100 filed Apr. 8, 2016, by inventors Michael T. Brubaker, Nathan Wray Matheny and Kurosh Nahavandi, the complete disclosure of which is incorporated herein by reference.

TECHNICAL FIELD AND BACKGROUND

The present disclosure relates to a cover for an opening, and more specifically to a cover for an opening in a medical apparatus.

In medical settings, it is often desirable to have attachment points or access points recessed within an apparatus. However, it is preferable that these attachment or access points be covered to facilitate cleaning.

SUMMARY OF THE INVENTION

Accordingly, the present disclosure describes a cover that can close or open an opening in an apparatus housing or covering to provide access to the opening, while still providing a surface that is easy to clean.

In one embodiment, a medical apparatus includes an apparatus body that has an opening and a cover coupled to the apparatus body about an axis of rotation angled to the surface about the opening in the apparatus body. The cover is operable to rotate about the axis of rotation to move between a first position wherein the cover closes the opening and a second position wherein the cover is moved to allow access to the opening.

In one aspect, the cover is coupled to the apparatus body by a cylindrical member. In a further aspect, the apparatus body has a transverse passageway for receiving the cylindrical member that is larger than the cylindrical member so that the cylindrical member can tilt in the transverse passageway.

According to another aspect, the cover is further coupled to the apparatus body by a fastener. In a further aspect, the fastener extends into the cylindrical member.

In yet another aspect, in any of the above, the medical apparatus may include a spring, with the spring biasing the cover into the first position.

In a further aspect, the spring is mounted about the axis of rotation.

In yet further aspects, the medical apparatus further includes a washer between the fastener and the cylindrical member. The spring is mounted about the cylindrical member between the washer and the apparatus body.

In another aspect, the cover includes a cover body. The apparatus body wall has a recess, which forms the opening, and a through hole. The cover body has a size and shape substantially equal to the size and shape of the recess.

In yet another aspect, the axis of rotation is offset in the opening, and the recess forms an enlarged shoulder adjacent the through hole.

In a further aspect, the cover is rotatably mounted to the enlarged shoulder.

In other aspects, the cover is flush with the apparatus body when moved to the first position.

In yet other aspects, the cover includes an engagement structure for engagement by (1) a tool or (2) a finger of a person.

In another aspect, the engagement structure comprises (1) a slot, (2) a recess, or (3) a high friction surface.

According to other aspects, the medical apparatus further includes a seal between the cover and the apparatus body when the cover is in the first position.

According to yet another aspect, the seal is mounted to the apparatus body about the through hole.

In another embodiment, the medical apparatus has an apparatus body with an opening. The cover includes a cover body having a cylindrical member depending therefrom along an axis of rotation angled to the surface about the opening. For example, the cylindrical member is configured to couple the cover body to the apparatus body about the axis of rotation and to allow the cover body to move between a first position to close the opening and a second position to allow access to the opening.

In another aspect, the cover is circular.

In yet another aspect, the cylindrical member includes a distal end, with the distal end having a threaded opening for receiving a fastener to secure the cover to the apparatus body.

In yet further aspects, the cover further includes a spring that biases the cover into the first position.

In other aspects, the cover further includes a fastener and a washer for positioning between the fastener and the cylindrical member. The spring mounts about the cylindrical member between the washer and the apparatus body when the cover is mounted to the apparatus body.

In yet other aspects, the cover body has a central axis orthogonal to the cover body, with the axis of rotation offset from the central axis.

In another aspect, the cover includes an engagement structure for engagement by (1) a tool or (2) a finger of a person.

In yet another aspect, the engagement structure comprises (1) a slot, (2) a recess, or (3) a high friction surface.

Accordingly, a cover is provided that can close an opening but also allows easy access to the opening, while providing a surface that is easy to clean.

These and other advantages and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE DRAWINGS

FIG. 1 is a perspective view of a medical apparatus with an opening cover;

FIG. 2 is a top perspective view of the opening cover of FIG. 1;

FIG. 3 is a bottom perspective view of the opening cover FIG. 2;

DETAILED DESCRIPTION

Figure 4:
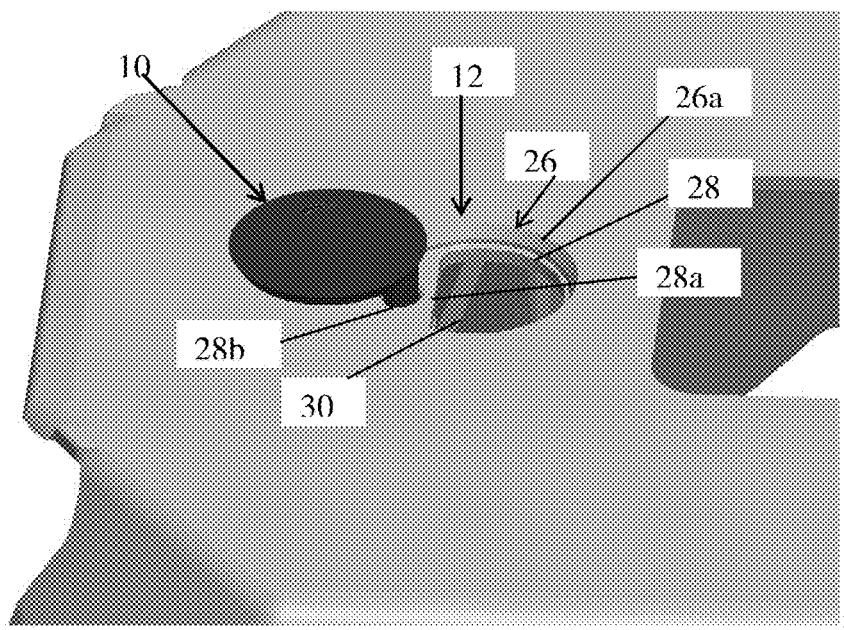
FIG. 4 is a similar view to FIG. 1 showing the cover moved away from the opening.

Referring to FIG. 1, the numeral 10 generally designates an opening cover, which is adapted to cover, and optionally seal, an opening 12 in an apparatus 14, such as a medical apparatus. As will be more fully described below, cover 10 is coupled to apparatus 14 so that it is movable between a first position in which the cover closes the opening 12 and a second position where the opening 12 is, at least partially if not entirely, uncovered and accessible.

As best seen in FIGS. 1-3, opening cover 10 includes a cover body 16 that includes a central axis 10a orthogonal to the cover body 16 and which is adapted to couple to body or housing 18 of apparatus 14 about an axis of rotation 20. Axis of rotation 20 is angled to the surface 12a about opening 12 so that the cover can rotate about the axis of rotation 20 to move between a first position wherein the cover 10 extends over and closes the opening 12 and a second position wherein the cover 10 is moved (e.g. to the side of opening 12) to allow access the opening 12. Further, as will be more fully described below, in one embodiment, axis of rotation 20 moves in a conical path so that cover 10 twists and spins out of opening 12 when it is moved to its second position.

As shown, in the illustrated embodiment, the axis of rotation 20 of the cover 10 is offset from the central axis 10a of cover 10 and, optionally, located at or near the edge of the cover, which further allows for the axis of rotation to be able to tip and have the cover ride freely out of the opening, as will be more fully understood from the description that follows. In the illustrated embodiment, cover body 16 is circular. However it should be understood that cover body 16 may have other shapes.

Referring again to FIGS. 2-3, cover 10 further includes a pivot member in the form of a cylindrical member 24. Cylindrical member 24 pivotally mounts cover 10 to apparatus 14 about axis 20 and, further, as will be more fully described below, retains cover 10 on apparatus 14. Cylindrical member 24 may be mounted to cover 10 or may be integrally formed therewith.

As best seen in FIG. 4, opening 12 is formed by a recess 26 in apparatus body 18. Optionally, recess 26 is formed in a wall 22 of apparatus body 18. However, it should be understood that cover 10 may be mounted to an apparatus body that is a solid body instead (such as shown and described in reference to FIG. 5B). Recess 26 forms a shoulder 28 and a through hole 30 that is offset in the recess 26 to form an enlarged shoulder 28a on one side of through hole 30. Enlarged shoulder 28a includes a transverse passageway 28b through which cylindrical member 24 extends for coupling cover 10 to apparatus body 18.

Figure 5:
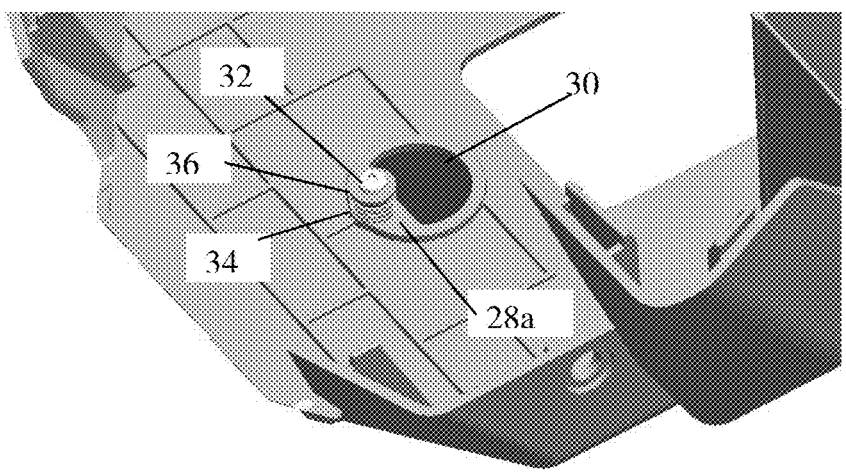
FIG. 5 is a bottom perspective view of the medical apparatus showing cover a similar view to FIG. 4.
Figure 5A:
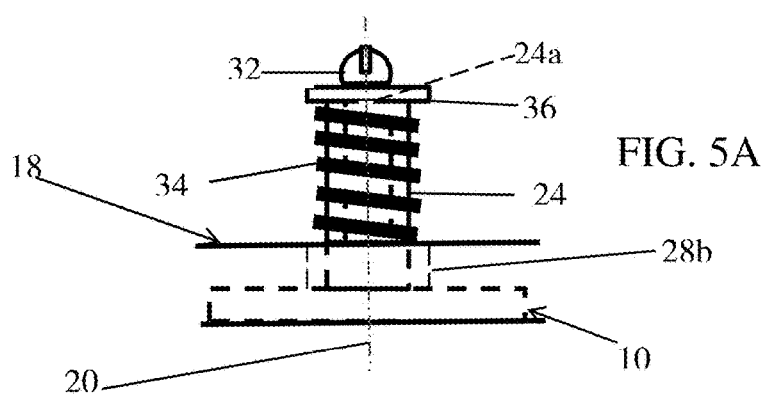
FIG. 5A is an enlarged view of the mounting details of the cover to the medical apparatus.

As understood from FIG. 5, cover 10 is further coupled to the apparatus body 18 by a fastener 32. As best seen in FIG. 5A, fastener 32 extends into the open threaded end 24a (FIG. 3) of cylindrical member 24, which extends through passageway 28b of enlarged shoulder 28a. Optionally, cover 10 further includes a spring 34 to bias the cover 10 toward apparatus body 18 and into its first position. For example, as best seen in FIG. 5A, the spring 34 is mounted about cylindrical member 24 and about the axis of rotation 20 of cover 10. Optionally, cover 10 includes a washer 36 (FIG. 5A) between the head of fastener 32 and apparatus body 18, with the spring 34 being mounted about the cylindrical member 24 between the washer 36 and the apparatus body 18.

As best seen in FIGS. 1 and 4, cover body 16 has a size and a shape that are substantially equal to the size and the shape of the recess 26 so that when cover body 16 is moved to its first position over opening 12, cover body 16 will seat in and fully close opening 12, and further seat on shoulder 28. In this manner, cover 10 effectively seals opening 12 when cover 10 is in its first position. Optionally, opening 12 may incorporate a seal about opening 12, such as O-ring seal, which may be seated on shoulder 28. Further, as best seen in FIGS. 1 and 4, when cover 10 is in its first position, cover body 16 is flush with apparatus body 18, which facilitates cleaning.

As noted above, axis 20 may move as cover 10 is moved between its first and second positions. For example, as best seen in FIG. 5A, passageway 28b may be sized greater than outside diameter of cylindrical member 24 to provide play between cylindrical member 24 and apparatus body 18. In this manner, as cover 10 is rotated out of opening 12, cylindrical member 24 will tilt in passageway 28b against the biasing force of the spring and axis 20 will move in a conical path so that cover 10 will tilt and twist out of opening 12.

As best in FIG. 2, cover 10 also includes an engagement structure 40 for engagement by (1) a tool or (2) a finger of a person. For example, a suitable engagement structure includes a (1) a slot, (2) a recess, or (3) a high friction surface. Further, the engagement structure 40 may be located offset from axis of rotation 20 so that when a force is applied by a person's finger or tool, cover 10 will pivot about axis of rotation 20. Alternately, the engagement structure 40 may align with the axis of rotation 20, for example, when configured to work with a tool, such as a screwdriver.

To facilitate rotation of cover 10 from its first position to its second position, cover body 16 may have a tapered edge 16a (FIGS. 3 and 4). Similarly, recess 26 may include a tapered side wall 26a (FIG. 4), which may have the same or similar taper to tapered edge 16a. Thus, tapered side wall 26a can guide cover 10 outwardly from recess 26 as cover 10 is rotated about axis of rotation 20. In other words, the interaction between the two tapers translates the rotational movement of the cover into sliding motion of the cover outwardly from recess 26 to thereby move the cover 10 out of the opening 12.

Cover 10 may be formed from a wide selection of materials, including plastic or metal or wood, or a composite material.

Figure 5B:
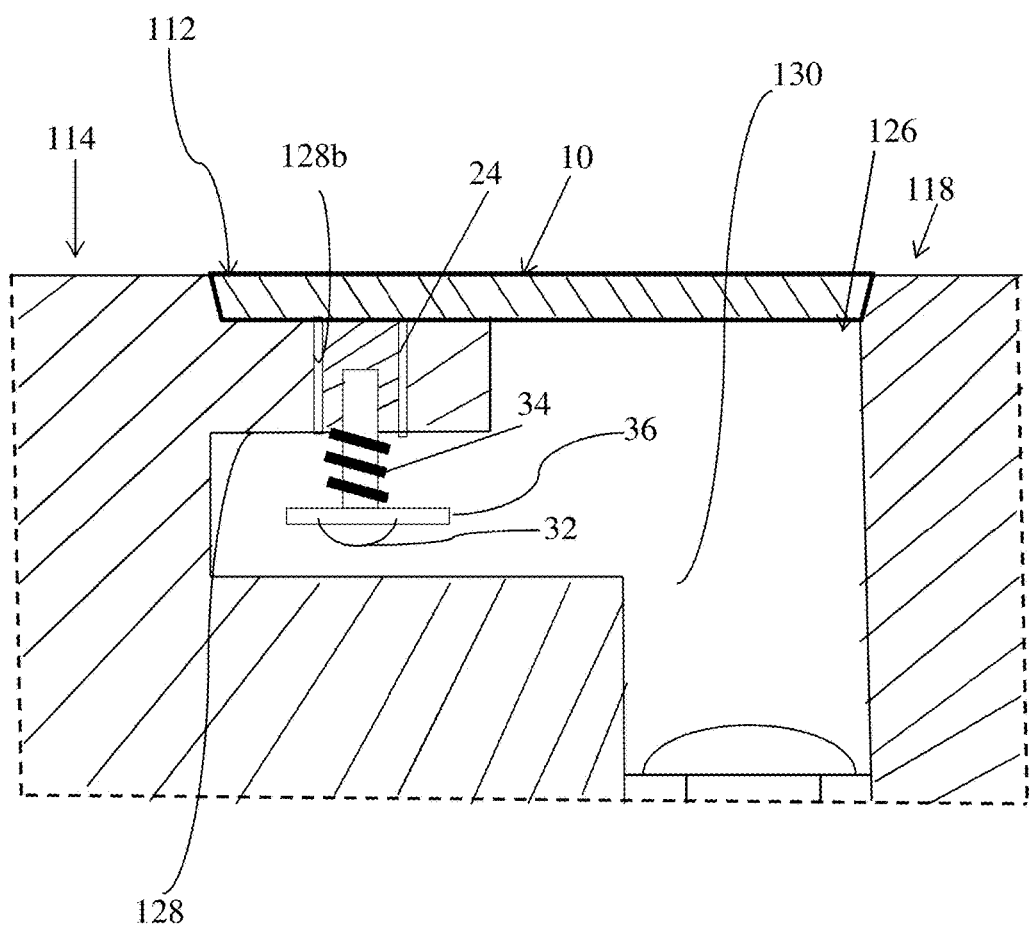
FIG. 5B is an enlarged view of another embodiment of the mounting details of the cover to a medical apparatus.

As noted above, cover 10 may be used on an apparatus with a solid apparatus body, such as shown in FIG. 5B. Referring to FIG. 5B, apparatus 114 includes an apparatus body 118 with an opening 112. Opening 112 is formed by a recess 126 that extends into the outer surface of apparatus body 118. Similar to recess 26, recess 126 forms a through hole 130 that forms an access opening or an attachment point that is recessed within apparatus 114.

Cover 10 is mounted in opening 112 on a flange 128, which extends into recess 126 to form a mounting surface for cover 10. Similar to shoulder 28, flange 128 includes a transverse passageway 128*b* for receiving cylindrical member 24 of cover 10. In a similar manner to the previous embodiment, cover 10 is secured in opening 112 by a fastener 32 and washer 36, with fastener 32 extending into and engaging the open end of cylindrical member 24. Spring 34 is similarly captured between washer 36 and the underside of flange 128 to apply a biasing force to cover 10. Again the size of passageway 128*b* may be greater than the cylindrical member 24 so that cylindrical member 24 can tilt in passageway to allow axis of rotation 20 to pivot and tilt, as described above. Similar to the previous embodiment, recess 126 may include a tapered perimeter to form a tapered interface with cover 10 to facilitate guiding cover 10 out of opening 112 when a force is applied to cover 10 by a finger or tool, as noted above. For further details of how cover 10 and apparatus body 118 cooperate, reference is made to the first embodiment.

Accordingly, cover 10 is configured to cover the opening and hole located in the opening, but is movable while remaining attached to the apparatus. Cover 10 is secured in place to cover the opening, but is allowed to pivot or spin out of position when rotated to thereby uncover the opening, and then rotated back into place. Receding the cover in place avoids unintended opening of the cover. Further, the spring applies a force to the cover that pulls it back into the opening. As noted, the angled interface between the cover and the respective opening allows for the cover to be guided out of the opening when a rotational force is applied and settle back into position in the opening when a rotational force is applied in the opposed direction. As described, the rotational force can be applied by a finger pressing on the engagement structure, such as an indent, which is offset from the rotational axis of the cover, or by way of a tool inserted into a slot, which may be offset as well or located above the rotational axis of the cover.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

We claim:

1. A medical apparatus comprising:
   an apparatus body having an apparatus body wall with an exterior surface, an orthogonal axis extending from said apparatus body orthogonal to said exterior surface, and a recess in said apparatus body wall, said recess including an opening at said exterior surface about said orthogonal axis and a through hole extending through said apparatus body wall, and said through hole being located in said recess; and
   a cover coupled to said apparatus body wall by a cylindrical member about a tiltable axis of rotation, said axis of rotation being tiltable relative to said orthogonal axis, said cylindrical member received in said opening to rotate said cover about said axis of rotation to move between a first position wherein said cover closes said opening and a second position wherein said cover tilts and rotates relative to said orthogonal axis and moves at least partially out of said opening to allow access to said opening, said cover having an exterior surface that faces outwardly from said apparatus body and is flush with said exterior surface of said apparatus body when said cover is moved to said first position wherein said recess forms a first recess, said apparatus body including a second recess accessible through said first recess, and said second recess for receiving an attachment device for forming an attachment point for said apparatus body.

2. The medical apparatus according to claim 1, wherein said apparatus body has a shoulder in said first recess, said shoulder including said through hole.

3. The medical apparatus according to claim 1, wherein said cylindrical member is coupled to said apparatus body by a fastener.

4. The medical apparatus according to claim 3, wherein said fastener extends into said cylindrical member.

5. The medical apparatus according to claim 4, further comprising a spring, said spring biasing said cover into said first position.

6. The medical apparatus according to claim 5, wherein said spring is mounted about said axis of rotation.

7. The medical apparatus according to claim 6, further comprising a washer between said fastener and said cylindrical member, and said spring being mounted about said cylindrical member between said washer and said apparatus body.

8. The medical apparatus according to claim 1, wherein said cover comprises a cover body, said first recess having a size and shape, and said cover body having a size and shape substantially equal to said size and shape of said first recess, and said cover body being imperforate.

9. The medical apparatus according to claim 8, further comprising a seal between said cover and said apparatus body when said cover is in said first position.

10. The medical apparatus according to claim 9, wherein said seal is mounted to said apparatus body wall about said opening.

11. The medical apparatus according to claim 1, wherein said cover includes an engagement structure for engagement by (1) a tool or (2) a finger of a person.

12. The medical apparatus according to claim 11, wherein said engagement structure comprises (1) a slot, (2) a recess, or (3) a high friction surface.

13. The medical apparatus according to claim 1, wherein said apparatus body includes a transverse passage, said cylindrical member extending through said through hole into said transverse passage to pivotally mount said cover to said apparatus body and forming said axis of rotation and said transverse passage being spaced from and about said cylindrical member wherein said axis of rotation tilts in said transverse passage when said cover is pivoted relative to said apparatus body.

14. A medical apparatus comprising:
  an apparatus body having an apparatus body wall with a recess, said apparatus body wall having an exterior surface, said recess forming an opening at said exterior surface, said recess having a recess diameter;
  a cover body having an outer perimeter, said cover body having a cylindrical member forming an axis of rotation inward of said outer perimeter, said outer perimeter defining a cover diameter generally equal to said recess diameter of said recess;
  said cover body configured to couple to said apparatus body about said axis of rotation and to move between a closed first position to close said opening and an open second position to allow access to said opening, said cover having an exterior surface that faces outwardly from said apparatus body and is flush with said exterior surface of said apparatus body when said cover is moved to said first position, and said cylindrical member having a length and extending below said apparatus body wall and to allow said cylindrical member and said cover body to tilt when said cover body pivots between said first position and said second position; and wherein said recess forms a first recess, said apparatus body including a second recess accessible through said first recess, and said second recess for receiving an attachment device for forming an attachment point for said apparatus body.

15. The medical apparatus according to claim 14, wherein said cover is circular.

16. The medical apparatus according to claim 14, said cover body further having a fastener, said fastener extending into said cylindrical member.

17. The medical apparatus according to claim 16, wherein said fastener comprises a threaded fastener, said cylindrical member comprising a threaded opening for receiving said fastener.

18. The medical apparatus according to claim 16, further comprising a spring, said spring to bias said cover into the first position.

19. The medical apparatus according to claim 18, further comprising a washer positioned between said fastener and said cylindrical member, and said spring mounted about said cylindrical member between said washer and said apparatus body.

20. The medical apparatus according to claim 14, wherein said cover body has a central axis orthogonal to said cover body, and said axis of rotation being offset from said central axis.

21. The medical apparatus according to claim 20, wherein said cover includes an engagement structure for engagement by (1) a tool or (2) a finger of a person.

22. The medical apparatus according to claim 21, wherein said engagement structure comprises (1) a slot, (2) a recess, or (3) a high friction surface.

23. The medical apparatus according to claim 14, wherein said cover comprises an imperforate cover body forming said exterior surface.

* * * * *